(12) United States Patent
Sham (10) Patent No.: US 9,931,053 B1
(45) Date of Patent: Apr. 3, 2018

(54) INTELLIGENT BABY CLOTHING WITH AUTOMATIC INFLATABLE NECK SUPPORT

(71) Applicant: Wellen Sham, Taipei (TW)

(72) Inventor: Wellen Sham, Taipei (TW)

(73) Assignee: Wellen Sham, Taipei (TW)

( * ) Notice: Subject to any disclaimer, the term of this patent is extended or adjusted under 35 U.S.C. 154(b) by 0 days.

(21) Appl. No.: 15/674,981

(22) Filed: Aug. 11, 2017

(51) Int. Cl.
*A61B 5/08* (2006.01)
*A61B 5/113* (2006.01)
*A61B 5/00* (2006.01)
*A41D 13/05* (2006.01)

(52) U.S. Cl.
CPC ............... *A61B 5/08* (2013.01); *A61B 5/113* (2013.01); *A61B 5/6804* (2013.01); *A41D 13/0512* (2013.01); *A61B 5/0002* (2013.01)

(58) Field of Classification Search
CPC ........................................ A61B 5/08
USPC ....... 340/573.1, 539.1, 539.11, 539.15; 2/69, 2/455
See application file for complete search history.

(56) References Cited

U.S. PATENT DOCUMENTS 5,937,443 A * 8/1999 Kageyama ........... A41D 13/018
2/455

* cited by examiner

*Primary Examiner* — Daryl Pope
(74) *Attorney, Agent, or Firm* — Kilpatrick Townsend & Stockton LLP (57) ABSTRACT

Embodiments provide a system to detect abnormal breathing by a person, such as a baby, through a piece of clothing worn by the person. The piece of clothing may be adapted to include a sound sensor that can collect breathing sounds by the person. The piece of clothing may also be adapted to include an inflatable neck support that can be automatically inflated without the person's intervention. The breathing sound signals by the person can be processed for determining whether the person breathing abnormally. When it is determined that the person is breathing abnormally, an instruction to inflate the inflatable neck support of the clothing may be generated. Such an instruction can be transmitted to the clothing wirelessly to effectuate the inflation of the inflatable neck support so the person's incorrect breathing posture that causes the abnormal breathing can be addressed.

18 Claims, 5 Drawing Sheets

INTELLIGENT BABY CLOTHING WITH AUTOMATIC INFLATABLE NECK SUPPORT

BACKGROUND OF THE INVENTION

This invention relates generally to personal safety systems and methods, and more particularly, to a systems and methods for monitoring a person, determining a person is breathing abnormally, and automatically addressing the abnormal breathing by the person.

Since the neck of an infant is not yet fully developed, bone and muscle strength in the infant's neck is typically not strong enough to support the infant's head. Typically, the weight of the infant's head accounts for a much larger percentage of the over-all weight of the body compared to an adolescent or an adult. In addition, infant's L skull is relatively large and its brain is relatively small, so its cranial cavity is not very stable. Numerous incidents have been found that incorrect breathing postures by an infant can cause bone or even brain damages to the infant, and in some severe instances even death of the infant.

The aforementioned breathing danger due to an infant's incorrect breathing posture may become even more acute when a care-giver of the infant is not paying attention to the infant. While the care-giver is supposed to keep an eye on the infant constantly, it is human nature that such attention may lapse from time to time. For example, the care-giver may be asleep while the infant is awake; or the care-giver may be on the phone or multi-tasking, and thus not providing enough attention to the infant. However, even the slightest lapse of the care-giver's attention to the infant could lead to a severe consequence if the infant was engaging in incorrect breathing postures during the lapse. In some circumstances, even if the care-giver is attentively caring for the infant, he/she may still not be aware the baby is engaging in incorrect breathing posture until it is too late. Moreover, in some situations, the care-giver may "over-cuddle" or "over-shake" the infant when the infant is crying. That could also contribute to incorrect breathing by the infant because the infant needs to compensate for the sudden stress caused by the "over-cuddling" or "over-shaking". Therefore there is a need to determine and address an incorrect breathing posture engaged in by an infant and/or notify the care-giver of such.

BRIEF SUMMARY OF THE INVENTION

In one aspect, embodiments can provide a system to detect abnormal breathing by a person, such as a baby, through a piece of clothing worn by the person. The piece of clothing may be adapted to include a sound sensor that can collect breathing sounds by the person. For example, the sound sensor may be attached to a collar of the clothing. The piece of clothing may also be adapted to include an inflatable neck support that can be automatically inflated without the person's intervention. In some implementations, the piece of clothing may also include a wireless transmitter that can transmit the breathing sound signals collected by the sound sensors to a remote processing device paired with the clothing. The remote processing device may be configured to process the sound signals and determine whether the person is breathing abnormally. When it is determined that the person is breathing abnormally, the remote processing device may be configured to generate an instruction to inflate the inflatable neck support of the clothing. Such an instruction can be transmitted to the clothing wirelessly to effectuate the inflation of the inflatable neck support so the abnormal breathing by the person due to his/her incorrect breathing posture can be addressed.

In some embodiments, the inflatable neck support of the clothing worn by the person may include a controllable inflation mechanism to allow the neck support to be inflated to a certain configuration. For example, the neck support may be inflated to more than one position to support the person's neck. In those embodiments, the remote processing device may be configured to determine a suitable inflated position for the neck support based on the abnormal breathing detected by the person as detected. In one embodiment, the remote processing device is configured to readjust the inflated position of the neck support based on one or more positions the inflatable neck support was inflated into previously.

In some embodiments, the remote processing device is configured to generate a notification after abnormal breathing by the person is detected. The notifications can be transmitted to a monitoring device associated with a care-giver of the person and may be implemented on the monitoring device to notify the care-giver of the abnormal breathing by the person. In some embodiments, the monitoring device associated with the care-giver can include a smart phone or a tablet device.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

DETAILED DESCRIPTION OF THE INVENTION

Figure 1:
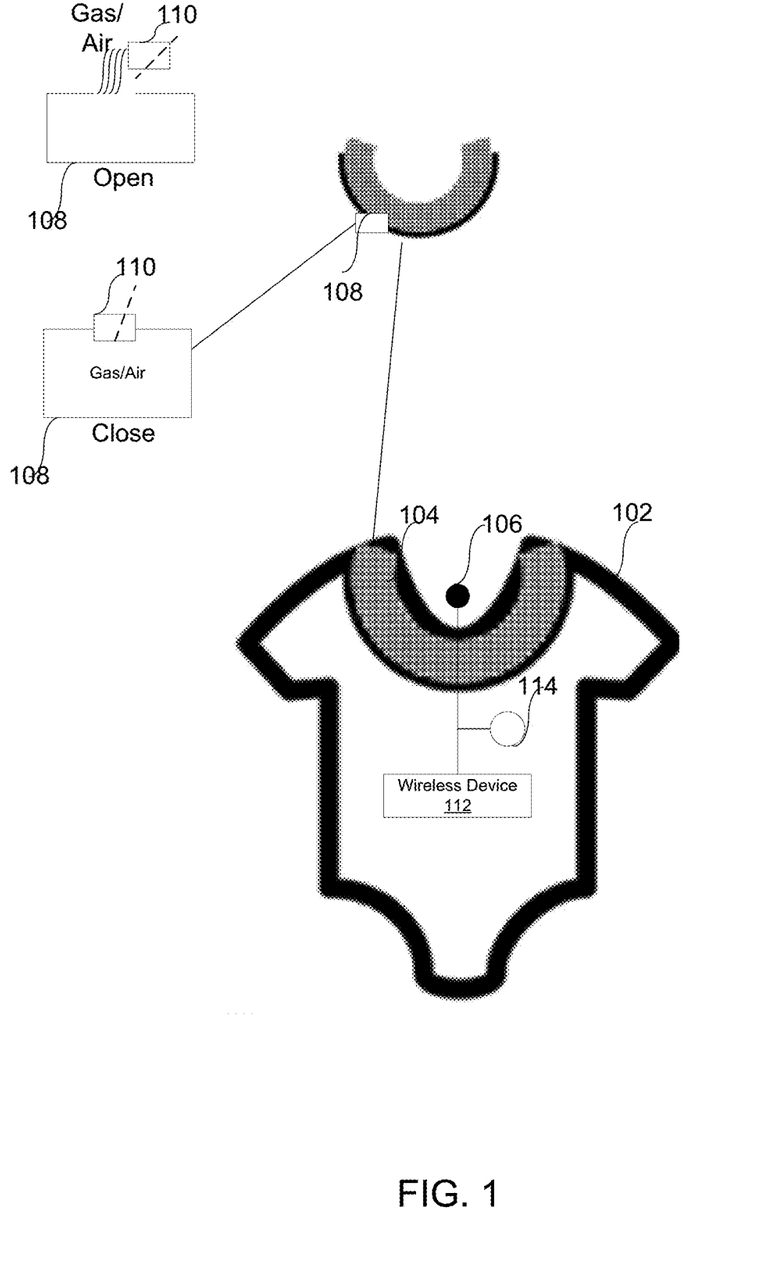
FIG. 1 illustrates one example of a piece of clothing that has a controllable and inflatable neck support in accordance with the disclosure.

For detecting, indicating and addressing abnormal breathing by a person such as a baby, an example of a piece of clothing in accordance with the disclosure is shown in FIG. 1. In this example, the piece of clothing 102 is illustrated as an overall that can be worn by a baby. This is not intended to be limiting. In some other examples, the piece of clothing may be in some other forms so long as it can be worn by a person. For example, the piece of clothing 102 may be a patient-gown that can be worn by a patient. It should be understood while "baby" is used throughout this disclosure, the age of the person that can wear clothing 102 is not intended to be limiting. It is contemplated that the clothing in accordance with the disclosure may be worn by an adolescent or an adult for detecting, indicating, and/or addressing abnormal breathing by the adolescent or the adult. For example, clothing 102 may be worn by an adult patient in comma.

As shown, the clothing 102 can include a U-shaped inflatable neck support 104 that can be inflated through a suitable means, such as air or gas, to support the baby's neck. The inflatable neck support 104 can be made of a thin fabric such as nylon. In various implementations, the inflatable neck support 104 may include a mechanism that can allow the inflatable neck support 104 to be inflated automatically without intervention from the person wearing clothing 102. In some implementations, the mechanism may include a controllable switch 110 that can be actuated to release gas or air contained in chamber 108 attached to inflatable neck support 104. It should be understood the illustration of chamber 108 is merely conceptual, and thus not intended to show the actual placement of the chamber 108 with respect to the inflatable neck support 104.

As shown in this example, there are may be two types of states associated with the inflatable neck support 104. In a "closed" state shown in FIG. 1, the switch 110 may be pushed into a position to completely seal the inflatable neck support 104 such that the interior of the chamber 108 is isolated from the atmosphere air. As illustrated, in the "closed" state, chamber 108 may be filled with fillable medium such as air or gas in a suitable concentration. The amount of the fillable medium and the type of the fillable medium are not limited by this disclosure. In some embodiments, gas such as nitrogen may be used and in some other embodiments air may be used. In any case, as shown, the controllable switch 110 may be actuated to leave an opening for the chamber 108. For example, the switch 110 may be sewed with one or more of a flexible string or a thread having a spring like property. The flexible string or thread can be connected to an actuation device (not shown), which may be controlled through a pulling mechanism responsive to mechanical touch. In implementations, the mechanical touch may be effectuated through an analog pulse which may be generated in response to a signal received from a processing device.

As also shown, as the switch 110 is removed from "closed" position to the "open" position, the fillable medium contained in chamber 108 may be released into inflatable neck support 104. This may be referred to as an "open" state of inflatable neck support 104. At the "closed" state, the inflatable neck support 104 may be deflated such that no or little fillable medium is left in inflatable neck support 104. During the "open" state, the fillable medium can be released into inflatable neck support 104 and thus inflate the inflatable neck support 104 to a certain position to support the person's neck.

In some implementations, the actuation device mentioned above may be configured to push the switch 110 from the open position to the close position after a certain time period, for example after 3 seconds. In those implementations, the clothing 102 may further include a timing device to measure such a time period and to effectuate the actuation device to "close" the switch 110 after the time period has elapsed. As will be described, the time period during which the inflatable neck support 104 remains open may also be controlled. Controlling such a time period can allow different amount of fillable medium to be released into the inflatable neck support 104 during the open state. Naturally, the longer this period is, the more fillable medium can be released into the inflatable neck support 104 and thus to form stronger support for the person's neck.

In some implementations, the switch 110 may include a suction device, such as a vacuum device, that can be activated to suck the fillable medium in the inflatable neck support 104 when the switch 110 is returned to the closed position. In those implementations, the switch 110 may be configured such that the fillable medium sucked from the inflatable neck support 104 can be released back into chamber 108 and thus can be used during next open state of inflatable neck support 104.

As still shown, the clothing 102 may include a sound sensor 106 configured to collect breathing sounds produced by the baby wearing the clothing 102. For collecting the breathing sounds of the person, a few factors need to be taken into account. First, the sound sensor 106 may not be very "sensitive" in picking up sound signals except for those produced the baby within close range where the sound sensor 106 is placed. In this way, noises may not be collected or may be reduced. Second, the sound sensor 106 may be connected to a power source such as batteries in order for it to be powered and running. In implementations, due to health hazards that may be associated with batteries, especially to a newborn, selection of the batteries for the clothing 102 needs extra care. Preferably, a button cell battery 114 as shown may be used for such a power source. In any case, the sound sensor 106 may be coupled to a wire that is capable for transmitting analog signals. In some implementations, the sound sensor 106 may be attached to the inflatable neck support 104 around the neck area of the baby.

In some implementations, the clothing 102 may also include a wireless device 112 that can transmit the sound signals collected by sound sensor 106 to a remote processing device. The wireless transmission device may employ any suitable wireless transmission technology such as Bluetooth, Near Field Communication (NFC), low radio frequency, WiFi and/or any other wireless technology. In implementations, the wireless device 114 may be powered by the same battery source that powers the sound sensor 106 as shown.

Figure 2:
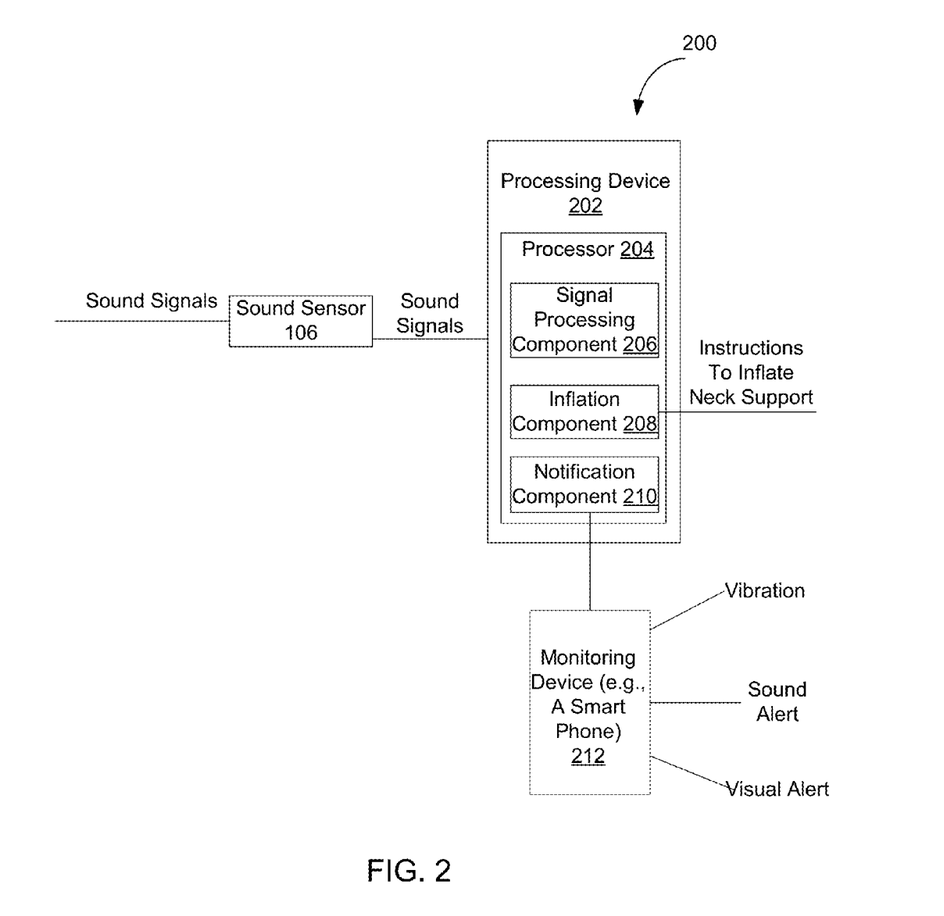
FIG. 2 illustrates one example of a system configured to control inflation of the inflatable neck support of the clothing shown in FIG. 1.

With an example of clothing 102 in accordance with the disclosure being generally described, attention is now directed to FIG. 2, where an example of a system 200 configured to control inflation of the clothing 102 is shown. It will be described with reference to FIG. 1. As shown, the system 200 may include a processing device 202 comprising one or more of a processor 204. In some implementations, the processing device 202 may include a desktop or a laptop computer that is paired with clothing 102 via Bluetooth link. Although not shown, the processing device 202 may include a communication module configured to communicate with clothing 102 and/or a monitoring device 212 associated with a care-giver (e.g., a parent or a nurse). As mentioned above, the communication module included in the processing device may employ any suitable wireless communication technology such as Bluetooth, NFC, low radio frequency or WiFi. In any case, as shown, the processor 204 may be configured to execute program components including a signal processing module 206, an inflation module 208, a notification module 210, and/or any other program components.

Figure 3A:
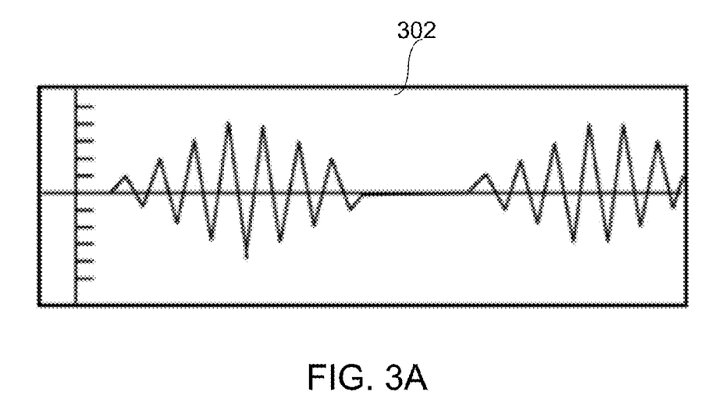
FIG. 3A illustrates one example of a current breathing pattern that can be stored in the system shown in FIG. 2.

The signal processing component 206 can be configured to process the breathing sound signals received from the sound sensor 106. As mentioned above, the clothing 102 may include a wireless device configured to transmit the breathing sound signals collected by the sound sensors 106 to the processing device 202. In some implementations, the transmission of the sound signals may be via Bluetooth. In any case, after receiving the breathing sound signals collected by the sound sensor 106, the signal processing component 206 may generate a current breathing pattern based on the received breathing sound signals. For example, the current breathing pattern may indicate breathing by the baby in the last 5 seconds. This current breathing pattern may be continuously updated as the breathing sound signals of the baby are continuously received from sound sensor 106. Generating the current breathing pattern by signal processing component 206 may include transcribing analog waveforms based on the volume of the sound signals received from the sound sensor 106. FIG. 3A illustrates one example of a current breathing pattern 302 that may be generated by the signal processing component 206. Of course, the breathing pattern 302 generated by the signal processing component 206 may be stored digitally in a memory storage associated with the processing device 202.

Figure 3B:
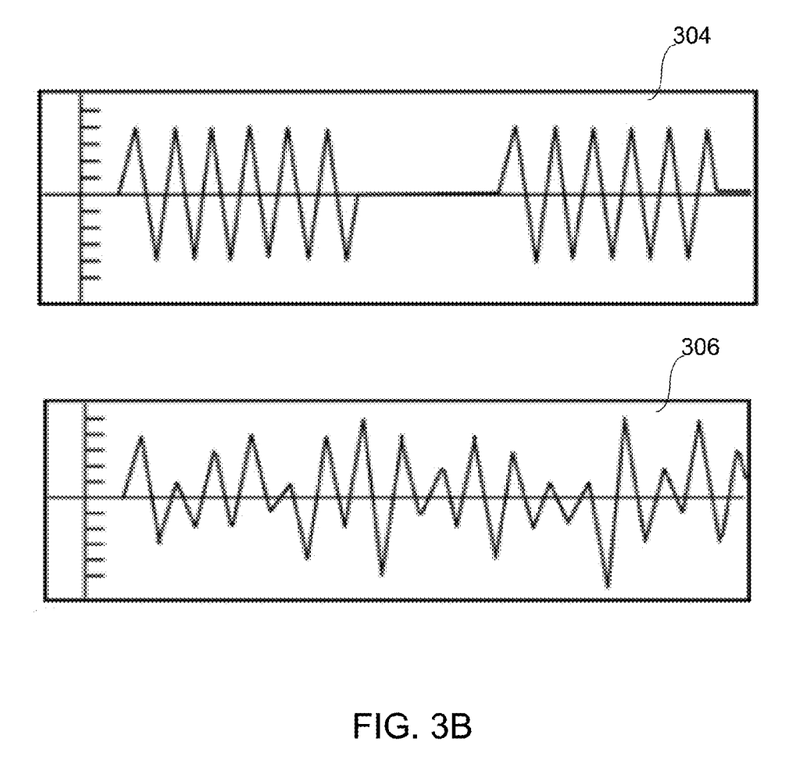
FIG. 3B illustrates two examples of abnormal breathing patterns that can be stored in the system shown in FIG. 2.

As the current breathing pattern 302 is being generated, the signal processing component 206 may be configured to compare the current breathing pattern 302 with one or more predetermined normal breathing patterns for the baby. The one or more predetermined normal breathing patterns may be collected by a doctor, a nurse or the care-giver when the baby is known to be breathing normally. In some implementations, the one or more normal breathing patterns of the baby may be collected using the sound sensor 106 and the clothing 102 in a recoding mode. FIG. 3B illustrates a couple of normal breathing patterns, i.e., 304 and 306 that can be collected. These breathing patterns can be stored in the memory storage associated with the processing device 202 and retrieved from the memory storage to enable the signal processing component 206 to compare the current breathing pattern 302 to them.

In some implementations, instead of or in addition to the predetermined normal breathing patterns, one or more abnormal breathing patterns may be stored in the memory storage associated with processing device. Such abnormal breathing patterns may be collected from babies that were known to have certain respiratory conditions, or may be simulated by a doctor to indicate abnormal breathing that can be had by a baby.

The breathing pattern comparison by signal processing component 206 may involve fitting the current breathing pattern 302 to the one or more predetermined normal breathing pattern, such as 304 and 306 as shown. The comparison can further include determining whether the current normal breathing pattern is conforming to the one or more predetermined normal breath patterns. In some implementations, such conformance may be determined by signal processing component 206 when a frequency of high low tidal volume of the breathing by the baby as indicated by the current breathing pattern 302 falls within a certain threshold with respect to the one or more predetermined normal breathing patterns. It should be understood that a perfect match of the patterns for determining whether the current breathing by the baby is not necessary. In certain implementations, the signal processing component 206 may be configured with such a threshold for determining the pattern conformance.

In some implementations, the signal processing component 206 may be configured to compare the current breathing pattern 302 to the one or more abnormal breathing patterns mentioned above. In those implementations, the signal processing component 206 may be configured to determine whether the current breathing pattern 302 is conforming to one of the one or more abnormal breathing patterns. In some implementations, the signal processing component 206 may be configured to first compare the current breathing pattern 302 with the one or more abnormal breathing patterns to determine whether the current breath pattern 302 conforms to one of the abnormal breathing patterns. In response to a determination that such a conformance is found, the signal processing component 206 may be configured to generate a signal indicating that the baby is breathing abnormally conforming to the known abnormal breathing pattern. In response to a determination that such a conformance is not found, the signal processing component 206 may be configured to further compare the current breathing pattern 302 with the one or more predetermined normal breathing patterns and to determine whether the current breathing pattern 302 conforms to the one or more predetermined normal breathing pattern. In response to such a conformance is not found, the signal processing component 206 may generate a signal indicating that the baby is not breathing normally but is not breathing in a way to cause a known respiratory condition.

Returning to FIG. 2, the inflation component 208 can be configured to generate an inflation instruction to effectuate inflation of the inflatable neck support 104 in accordance with the abnormal breathing detected by the signal processing component 206. The inflation instruction generated by the inflation component 208 may indicate a position or configuration of the inflatable neck support 104 should be inflated into. For example, as described above, signal processing component 206 may generate a signal indicating that the baby is breathing abnormally in a known incorrect breathing posture. In response to such a signal, the inflation component 208 may generate the inflation instruction to enable the inflatable neck support 104 to be inflated into a preset position or configuration that can address or correct the breathing posture. For example, such a preset position may correspond to a certain percentage of the fillable medium in the chamber 108 to be released into inflatable neck support 104 to inflate the inflatable neck support 104; and/or a certain time period (e.g., 3 seconds) the inflatable neck support 104 should be in the "open" state. Different abnormal breathing patterns may be associated with different positions for addressing them. These different positions may be programmed into inflation component 208 during a configuration stage or an update stage of the processing device 202.

In some implementations, a default position may programmed into the inflation component 208 such that when an unknown abnormal breathing pattern is detected by the signal processing component 206, the signal processing component 206 may generate the inflation instruction to inflate the inflatable neck support 104 into the default position. The default position of the inflated neck support 104 may be a position that is relatively "safe" for the baby, for example 50% inflated. In some implementations, the inflation component 208 may be configured to "remember" one or more previous positions it has instructed the inflatable neck support 104 to be inflated into. In those implementations, the inflation component 208 may be configured to adjust the inflated positions that the inflatable neck support 104 is already in when abnormal breathing pattern continues to be detected by signal processing component 206.

By way of example, when a general abnormal breathing pattern is first detected by signal processing component 206, the inflation component 208 may generate an inflation instruction to instruct the inflatable neck support 104 to inflate into a first position—e.g., 50% inflated. Subsequently, if the signal processing component 206 continues to detect the general abnormal breathing pattern by the baby, the inflation component 208 may generate another inflation instruction to instruct the inflatable neck support 104 to inflate into a second position based on the first position— e.g., 60% inflated. If the signal processing component 206 still continues to detect the general abnormal breathing pattern by the baby, the inflation component 208 may generate yet another inflation instruction to instruct the inflatable neck support 104 to inflate into a third position based on the second position—e.g., 70% inflated. This cycle can continue until abnormal breathing pattern is no longer detected by signal processing component 206 or the clothing 102 is deactivated by the care-giver.

As should be already clear, the inflation instruction generated by the inflation component 208 can be transmitted wirelessly to the clothing 102 via the wireless device 114 shown in FIG. 1. Upon receiving such an inflation instruction from the processing device 102, the inflatable neck support 104 may be automatically inflated in accordance with the received inflation instruction. For example, actuation device described above can be automatically and mechanically controlled in accordance with the inflation instruction received from processing device 102.

The notification component 210 can be configured to generate a notification indicating the baby is breathing abnormally in response to the abnormal breathing pattern by the baby is detected by signal processing component 206. The notification generated by the notification component 210 may include information indicating a timestamp when the baby was first detected to be breathing abnormally, how long the baby was detected to have been breathing abnormally, a known abnormal breathing pattern indicating a corresponding respiration condition (if detected by signal processing component 206 as described above), and/or any other information. In some implementations, the notification generated by notification component 210 may include information indicating a number of times the inflatable neck support 104 has been inflated into different positions due to continuous detection of abnormal breathing by the baby.

The notification generated by the notification component 210 can be transmitted to a monitoring device associated with a care-giver of the baby, such as the monitoring device 212 shown in FIG. 2. In some implementations, the monitoring device 212 may include a smart phone, a tablet device, a laptop or any other portable computing device. The notification from the notification component 210 can be implemented on the monitoring device 212 to notify the care-giver that the baby is breathing abnormally. In some implementations, the notification can be implemented to vibrate the monitoring device 212, to make a sound alert through the monitoring device 212, and/or to display a visual alert on the monitoring device 212. For example, when the notification indicates that the inflatable neck support 104 has been inflated and abnormal breathing pattern by the baby is no longer detected after the inflation, a vibration of the monitoring device 212 may be generated to gently remind the care-giver to check on the baby and to manually deflate the inflatable neck support 104 if necessary. Still as an example, when the notification indicates that the inflatable neck support 104 has been inflated into different positions due continuous unknown abnormal breathing pattern by the baby is detected and one or more vibrations or sound alert have been made through the monitoring device 212, a very loud and continuous sound alert may be generated to alert the care-giver. This may be desired because such a situation may indicate the care-giver is not aware the baby is breathing abnormally. The visual alert may include information indicating various aspects regarding the abnormal breathing pattern by the baby as described above. This can help the care-giver to quickly gain knowledge of the abnormal breathing by the baby.

Figure 4:
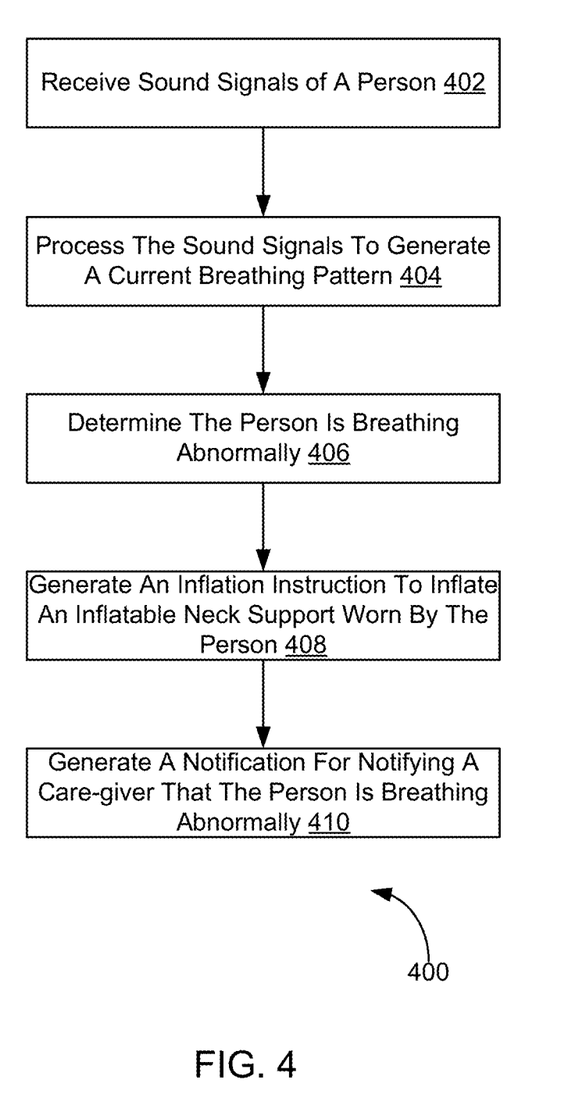
FIG. 4 illustrates one exemplary method for controlling inflation of the inflatable neck support of the clothing shown in FIG. 1 and for notifying of such to a care-giver.

Attention is now is directed to FIG. 4 which illustrates an exemplary method 400 for controlling inflation of the inflatable neck support of the clothing shown in FIG. 1 and for notifying of such to a care-giver. The particular series of processing steps depicted in FIG. 4 is not intended to be limiting. It is appreciated that the processing steps may be performed in an order different from that depicted in FIG. 4 and that not all the steps depicted in FIG. 4 need be performed. In certain implementations, the method 400 may be implemented by a video processing center, such as the video processing center shown in FIG. 5.

In some embodiments, the method depicted in method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At 402, sound signals of a person, such as a baby can be received. As described and illustrated herein, a piece of clothing such as clothing 102 shown in FIG. 1 can be worn by the person. The piece of clothing can include an inflatable neck support, a sound sensor, a wireless device and/or any other components. The sound sensor can be attached to the clothing such that it can collect breathing sounds of the person. The sound signals collected by the sound sensor can be received at 402 at a remote processing device paried with clothing 102 via Bluthtooth. In some implementations, operations invovled in 402 can be implemented by a signal processing component the same as or substantially similar to signal processing component 206 described and illustrated herein.

At 404, the sound signals received at 402 can be processed to generate a current breathing pattern of the person. The current breathing pattern generated at 404 may indicate breathing by the baby in the last a few seconds. This current breathing pattern may be continuously updated as the sound signals are continuously received at 402. Generating the current breathing pattern at 404 may include transcribing analog waveforms based on the volume of the sound signals received at 402. FIG. 3A illustrates one example of a current breathing pattern 302 that may be generated at 404. In some implementations, operations invovled in 404 can be implemented by a signal processing component the same as or substantially similar to signal processing component 206 described and illustrated herein.

At 406, a determination that the person is breathing abnormally may be made. The determination made at 406 may invovle comparing the current breathing pattern generated at 404 with one or more predetermined normal breathing patterns of the person. The one or more predetermined normal breathing patterns of the person may be collected by a doctor, a nurse or the care-giver when the person is known to be breathing normally. In some implementations, the one or more normal breathing patterns of the person may be collected using the sound sensor 106 and the clothing 102 in a recoding mode. FIG. 3B illustrates a couple of normal breathing patterns, i.e., 304 and 306 that can be collected. The comparison of the breathing patterns can include determining whether the current normal breathing pattern generated at 404 is conforming to the one or more predetermined normal breath patterns. Such conformance may be found when a frequency of high low tidal volume of the breathing by the person as indicated by the current breathing pattern generated at 404 falls within a certain threshold with respect to the one or more predetermined normal breathing patterns.

In some implementations, the determination made at 406 may involve comparing the current breathing pattern generated at 404 with one or more predetermined abnormal breathing patterns of the person. The abnormal breathing patterns of the person may be collected from people that were known to have certain respiratory conditions, or may be simulated by a doctor to indicate abnormal breathing that can be had by a person. In some implementations, the determination at 406 may first involve comparing the current breathing pattern generated at 404 with the one or more abnormal breathing patterns to determine whether the current breath pattern conforms to one of the abnormal breathing patterns. In response to a determination that such a conformance is found, a determination indicating that the person is breathing abnormally conforming to the known abnormal breathing pattern can be made. In response to a determination that such a conformance is not found, the current breathing pattern generated at 404 can be compared with the one or more predetermined normal breathing patterns for determining whether the current breathing pattern conforms to the one or more predetermined normal breathing pattern. In response to such a conformance is not found, a determination that the person is generally breathing abnormally (i.e., breathing abnormally in an unknown way) can be made. In some implementations, operations invovled in 406 can be implemented by a signal processing component the same as or substantially similar to signal processing component 206 described and illustrated herein.

At 408, an inflation instruction to inflate a inflatable neck support included in the clothing worn by the person can be made in response to the determination made at 406. The inflation instruction generated by at 408 may indicate a position or configuration of the inflatable neck support should be inflated into. For example, as described above, a determination indicating that the baby is breathing abnormally in a known incorrect breathing posture may be made at 408. In response to such a determination, the inflation instruction may be generated at 408 to enable the inflatable neck support of the clothing shown in FIG. 1 to be inflated into a preset position or configuration that can address or correct the breathing posture. For example, such a preset position may correspond to a certain percentage of the fillable medium in the chamber to be released into inflatable neck support to inflate the inflatable neck support; and/or a certain time period (e.g., 3 seconds) the inflatable neck support 104 should be in the "open" state. The inflation instruction generated by at 408 can be transmitted wirelessly to the clothing worn by the person via the wireless device shown in FIG. 1. Upon receiving such an inflation instruction, the inflatable neck support of the clothing as shown in FIG. 1 may be automatically inflated in accordance with the received inflation instruction. In some implementations, operations invovled in 408 can be implemented by inflation component the same as or substantially similar to a inflation component 208 described and illustrated herein.

At 410, a notification for notifying a care-giver that the person is breathing abnormally can be generated in response to determination made at 406. The notification generated at 410 may include information indicating a timestamp when the person was first detected to be breathing abnormally, how long the person was detected to have been breathing abnormally, a known abnormal breathing pattern indicating a corresponding respiration condition (if determined at 406 as described above), and/or any other information. In some implementations, the notification generated at 410 may include information indicating a number of times the inflatable neck support has been inflated into different positions due to continuous detection of abnormal breathing by the person. The notification generated at 410 can be transmitted to a monitoring device associated with the care-giver, such as the monitoring device 212 shown in FIG. 2. The notification can be implemented on such a monitoring device to notify the care-giver that the person is breathing abnormally. In some implementations, the notification can be implemented to vibrate the monitoring device, to make a sound alert through the monitoring device, and/or to display a visual alert on the monitoring device. In some implementations, operations invovled in 410 can be implemented by a notification component the same as or substantially similar to a notification component 210 described and illustrated herein.

Figure 5:
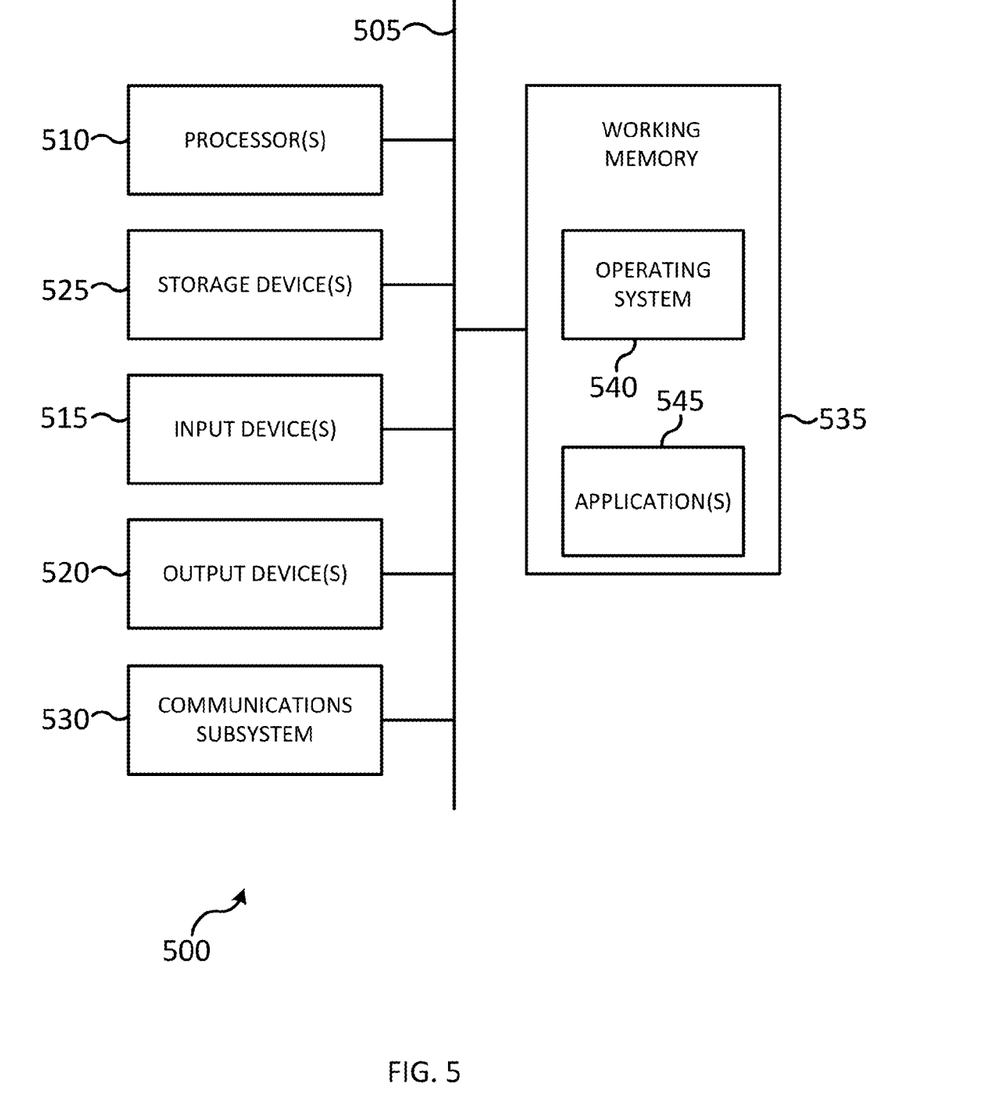
FIG. 5 illustrates one example of a computer system that can be used to implement various embodiments described and illustrated herein.

FIG. 5 illustrates a simplified computer system that can be used implement various embodiments described and illustrated herein. A computer system 500 as illustrated in FIG. 5 may be incorporated into devices such as a portable electronic device, mobile phone, or other device as described herein. FIG. 5 provides a schematic illustration of one embodiment of a computer system 500 that can perform some or all of the steps of the methods provided by various embodiments. It should be noted that FIG. 5 is meant only to provide a generalized illustration of various components, any or all of which may be utilized as appropriate. FIG. 5, therefore, broadly illustrates how individual system elements may be implemented in a relatively separated or relatively more integrated manner.

The computer system 500 is shown comprising hardware elements that can be electrically coupled via a bus 505, or may otherwise be in communication, as appropriate. The hardware elements may include one or more processors 510, including without limitation one or more general-purpose processors and/or one or more special-purpose processors such as digital signal processing chips, graphics acceleration processors, and/or the like; one or more input devices 515, which can include without limitation a mouse, a keyboard, a camera, and/or the like; and one or more output devices 520, which can include without limitation a display device, a printer, and/or the like.

The computer system 500 may further include and/or be in communication with one or more non-transitory storage devices 525, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

The computer system 500 might also include a communications subsystem 530, which can include without limitation a modem, a network card (wireless or wired), an infrared communication device, a wireless communication device, and/or a chipset such as a Bluetooth™ device, an 502.11 device, a WiFi device, a WiMax device, cellular communication facilities, etc., and/or the like. The communications subsystem 530 may include one or more input and/or output communication interfaces to permit data to be exchanged with a network such as the network described below to name one example, other computer systems, television, and/or any other devices described herein. Depending on the desired functionality and/or other implementation concerns, a portable electronic device or similar device may communicate image and/or other information via the communications subsystem 530. In other embodiments, a portable electronic device, e.g. the first electronic device, may be incorporated into the computer system 500, e.g., an electronic device as an input device 515. In some embodiments, the computer system 500 will further comprise a working memory 535, which can include a RAM or ROM device, as described above.

The computer system 500 also can include software elements, shown as being currently located within the working memory 535, including an operating system 540, device drivers, executable libraries, and/or other code, such as one or more application programs 545, which may comprise computer programs provided by various embodiments, and/or may be designed to implement methods, and/or configure systems, provided by other embodiments, as described herein. Merely by way of example, one or more procedures described with respect to the methods discussed above, such as those described in relation to FIG. 5, might be implemented as code and/or instructions executable by a computer and/or a processor within a computer; in an aspect, then, such code and/or instructions can be used to configure and/or adapt a general purpose computer or other device to perform one or more operations in accordance with the described methods.

A set of these instructions and/or code may be stored on a non-transitory computer-readable storage medium, such as the storage device(s) 525 described above. In some cases, the storage medium might be incorporated within a computer system, such as computer system 500. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by the computer system 500 and/or might take the form of source and/or installable code, which, upon compilation and/or installation on the computer system 500 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware, software including portable software, such as applets, etc., or both. Further, connection to other computing devices such as network input/output devices may be employed.

As mentioned above, in one aspect, some embodiments may employ a computer system such as the computer system 500 to perform methods in accordance with various embodiments of the technology. According to a set of embodiments, some or all of the procedures of such methods are performed by the computer system 500 in response to processor 510 executing one or more sequences of one or more instructions, which might be incorporated into the operating system 540 and/or other code, such as an application program 545, contained in the working memory 535. Such instructions may be read into the working memory 535 from another computer-readable medium, such as one or more of the storage device(s) 525. Merely by way of example, execution of the sequences of instructions contained in the working memory 535 might cause the processor(s) 510 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using the computer system 500, various computer-readable media might be involved in providing instructions/code to processor(s) 510 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 525. Volatile media include, without limitation, dynamic memory, such as the working memory 535.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 510 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 500.

The communications subsystem 530 and/or components thereof generally will receive signals, and the bus 505 then might carry the signals and/or the data, instructions, etc. carried by the signals to the working memory 535, from which the processor(s) 510 retrieves and executes the instructions. The instructions received by the working memory 535 may optionally be stored on a non-transitory storage device 525 either before or after execution by the processor(s) 510.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a schematic flowchart or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of steps may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a user" includes a plurality of such users, and reference to "the processor" includes reference to one or more processors and equivalents thereof known to those skilled in the art, and so forth.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A system for child safety, the system comprising one or more of a processor configured to execute machine-readable instructions such that when the machine-readable instructions are executed to cause the one or more processors to perform:
   receiving breathing sound signals of a baby collected by a sound sensor included in a piece of clothing worn by the baby, the baby clothing including an inflatable neck support;
   processing the breathing sound signals to generate a current breathing pattern for the baby;
   determining whether the baby is breathing abnormally by comparing the current breathing pattern with one or more predetermined normal breathing patterns of the baby;
   in response to a determination that the baby is breathing abnormally, generating an inflation instruction to inflate the inflatable neck support of the baby clothing; and
   transmitting the inflation instruction wirelessly to the baby clothing to effectuate the inflation of the inflatable neck support of the baby clothing.

2. The system of claim 1, wherein the one or more processors are further configured by the machine-readable instructions to:
   in response to the generation of the inflation instruction, generating a notification for notifying a care-giver of the baby that the baby is breathing abnormally; and
   transmitting the notification wirelessly to a monitoring device associated with the care-giver to effectuate the notification to the care-giver.

3. The system of claim 2, wherein the effectuation of the notification includes at least one of vibrating the monitoring device associated with the care-giver, making a sound alert through the monitoring device associated with the care-giver, and displaying a visual alert on the monitoring device associated with the care-giver.

4. The system of claim 2, wherein the notification indicating at least one of when the abnormal breathing by the baby is first detected, how long the baby is detected to be breathing abnormally, and whether inflatable neck support has been instructed to be inflated.

5. The system of claim 1, wherein the determination whether the baby is breathing abnormally is performed by further comparing the current breathing pattern of the baby with one or more stored abnormal breathing patterns corresponding know respiration conditions.

6. The system of claim 5, further comprising determining whether the baby is having one of the known respiration conditions.

7. The system of claim 6, the generation of the inflation instruction is based on the respiration condition the baby is determined to be having when the baby is determined to be having the respiration condition.

8. The system of claim 1, wherein the inflation instruction includes information indicating a percentage of inflation the inflatable neck support should be inflated into, and/or a duration for which a Tillable medium is to be released into the inflatable neck support to inflate the inflatable neck support.

9. The system of claim 1, wherein the generation of instruction is based on one or more previously generated inflation instructions.

10. A method for controlling inflation of inflatable neck support of a piece of clothing worn by a baby, the method being implemented by a processor, the method comprising:
   receiving breathing sound signals of a baby collected by a sound sensor included in the piece of clothing worn by the baby;
   processing the sound signals to generate a current breathing pattern for the baby;
   determining whether the baby is breathing abnormally by comparing the current breathing pattern with one or more predetermined normal breathing patterns of the baby;
   in response to a determination that the baby is breathing abnormally, generating an inflation instruction to inflate the inflatable neck support of the baby clothing; and transmitting the inflation instruction wirelessly to the baby clothing to effectuate the inflation of the inflatable neck support of the baby clothing.

11. The method of claim 10, further comprising
in response to the generation of the inflation instruction, generating a notification for notifying a care-giver of the baby that the baby is breathing abnormally; and
transmitting the notification wirelessly to a monitoring device associated with the care-giver to effectuate the notification to the care-giver.

12. The method of claim 11, wherein the effectuation of the notification includes at least one of vibrating the monitoring device associated with the care-giver, making a sound alert through the monitoring device associated with the care-giver, and displaying a visual alert on the monitoring device associated with the care-giver.

13. The method of claim 11, wherein the notification indicating at least one of when the abnormal breathing by the baby is first detected, how long the baby is detected to be breathing abnormally, and whether inflatable neck support has been instructed to be inflated.

14. The method of claim 10, wherein the determination whether the baby is breathing abnormally is performed by further comparing the current breathing pattern of the baby with one or more stored abnormal breathing patterns corresponding know respiration conditions.

15. The method of claim 14, further comprising determining whether the baby is having one of the known respiration conditions.

16. The method of claim 15, the generation of the inflation instruction is based on the respiration condition the baby is determined to be having when the baby is determined to be having the respiration condition.

17. The method of claim 10, wherein the inflation instruction includes information indicating a percentage of inflation the inflatable neck support should be inflated into, and/or a duration for which a fillable medium is to be released into the inflatable neck support to inflate the inflatable neck support.

18. The method of claim 10, wherein the generation of instruction is based on one or more previously generated inflation instructions.

* * * * *